(12) United States Patent
Kashani et al.

(10) Patent No.: US 10,010,447 B2
(45) Date of Patent: Jul. 3, 2018

(54) SYSTEMS AND METHODS FOR SUBRETINAL DELIVERY OF THERAPEUTIC AGENTS

(71) Applicant: Novartis AG, Basel (CH)

(72) Inventors: Pooria S. Kashani, Irvine, CA (US); Michael Papac, North Tustin, CA (US)

(73) Assignee: Novartis AG, Basel (CH)

( * ) Notice: Subject to any disclaimer, the term of this patent is extended or adjusted under 35 U.S.C. 154(b) by 1023 days.

(21) Appl. No.: 14/132,859

(22) Filed: Dec. 18, 2013

(65) Prior Publication Data

US 2015/0164687 A1    Jun. 18, 2015

(51) Int. Cl.
| | | |
|---|---|---|
| *A61F 9/00* | (2006.01) | |
| *A61M 5/178* | (2006.01) | |
| *A61M 5/32* | (2006.01) | |
| *A61B 17/00* | (2006.01) | |

(52) U.S. Cl.
CPC .......... *A61F 9/0017* (2013.01); *A61F 9/0008* (2013.01); *A61M 5/178* (2013.01); *A61M 5/32* (2013.01); *A61B 17/00491* (2013.01)

(58) Field of Classification Search
CPC .......... A61M 2210/0612; A61F 9/0008; A61F 9/00781; A61B 17/00491; A61L 24/00
USPC .......................................................... 604/22
See application file for complete search history.

(56) References Cited

U.S. PATENT DOCUMENTS

| | | | |
|---|---|---|---|
| 5,084,009 A | * | 1/1992 | Mackool ............. A61M 1/0084 604/22 |
| 5,164,188 A | | 11/1992 | Wong |
| 5,273,530 A | | 12/1993 | del Cerro et al. |
| 5,399,352 A | | 3/1995 | Hanson |
| 5,409,457 A | | 4/1995 | del Cerro et al. |
| 5,443,505 A | | 8/1995 | Wong et al. |
| 5,632,984 A | | 5/1997 | Wong et al. |

(Continued)

FOREIGN PATENT DOCUMENTS

| | | |
|---|---|---|
| AU | 2011218623 | 9/2011 |
| AU | 2011221361 | 9/2011 |

(Continued)

OTHER PUBLICATIONS

PCT Search Report and Written Opinion dated Aug. 4, 2015 issued in PCT/US2014/064407.

(Continued)

*Primary Examiner* — Andrew Gilbert
*Assistant Examiner* — William Frehe (57) ABSTRACT

A retinal treatment system for delivering therapeutic agents to a target location with a retina is disclosed herein. The retinal treatment system includes a console having a control system and a handheld device coupled to the control system. The handheld device includes an inner tube disposed within an outer tube and being axially moveable within the outer tube. The inner tube has a perforating tip that is configured to perforate an inner limiting membrane of the retina. The handheld device further includes a chamber coupled to a proximal end of the inner tube that is configured to receive a fluid containing therapeutic agents injectable from the perforating tip. The control system of the retinal treatment system permits a user to maintain a position of the handheld device relative to the retina and activate an injection of a portion of the fluid through the inner tube into the retina.

22 Claims, 7 Drawing Sheets

(56) References Cited

U.S. PATENT DOCUMENTS

| | | | |
|---|---|---|---|
| 5,755,700 A * | 5/1998 | Kritzinger | A61F 9/00736 604/257 |
| 5,766,242 A | 6/1998 | Wong et al. | |
| 5,767,079 A | 6/1998 | Glaser et al. | |
| 5,824,072 A | 10/1998 | Wong | |
| 5,948,427 A | 9/1999 | Yamamoto et al. | |
| 5,952,378 A | 9/1999 | Stjernschantz et al. | |
| 5,985,307 A | 11/1999 | Hanson et al. | |
| 6,015,403 A | 1/2000 | Jones | |
| 6,149,931 A | 11/2000 | Schwartz et al. | |
| 6,219,575 B1 | 4/2001 | Nemati | |
| 6,306,074 B1 | 10/2001 | Waksman et al. | |
| 6,309,374 B1 | 10/2001 | Hecker et al. | |
| 6,334,856 B1 | 1/2002 | Allen et al. | |
| 6,378,526 B1 | 4/2002 | Bowman et al. | |
| 6,397,849 B1 | 6/2002 | Bowman et al. | |
| 6,413,245 B1 | 7/2002 | Yaacobi et al. | |
| 6,489,350 B1 | 12/2002 | Benedyk | |
| 6,491,670 B1 | 12/2002 | Toth et al. | |
| 6,696,415 B2 | 2/2004 | Gendron et al. | |
| 6,743,211 B1 | 6/2004 | Prausnitz et al. | |
| 6,936,053 B1 | 8/2005 | Weiss | |
| 6,945,984 B2 | 9/2005 | Arumi et al. | |
| 7,141,048 B1 | 11/2006 | Charles | |
| 7,207,980 B2 | 4/2007 | Christian et al. | |
| 7,285,107 B1 | 10/2007 | Charles | |
| 7,344,499 B1 | 3/2008 | Prausnitz et al. | |
| 7,699,882 B2 | 4/2010 | Stamper et al. | |
| 7,846,123 B2 | 12/2010 | Vassiliades et al. | |
| 7,909,800 B2 | 3/2011 | Cazzini | |
| 7,918,814 B2 | 4/2011 | Prausnitz et al. | |
| 7,931,596 B2 | 4/2011 | Rachlin et al. | |
| 7,967,772 B2 | 6/2011 | McKenzie et al. | |
| 8,034,105 B2 | 10/2011 | Stegmann et al. | |
| 8,057,483 B2 | 11/2011 | Aramant et al. | |
| 8,123,729 B2 | 2/2012 | Yamamoto et al. | |
| 8,147,512 B1 | 4/2012 | Puskas et al. | |
| 8,172,830 B2 | 5/2012 | Christian et al. | |
| 8,177,747 B2 | 5/2012 | Pinedjian | |
| 8,197,435 B2 | 6/2012 | Prausnitz et al. | |
| 8,348,924 B2 | 1/2013 | Christian et al. | |
| 8,425,473 B2 | 4/2013 | Ho et al. | |
| 8,535,268 B2 | 9/2013 | Auld et al. | |
| 8,636,713 B2 | 1/2014 | Prausnitz et al. | |
| 8,808,225 B2 | 8/2014 | Prausnitz et al. | |
| 9,220,631 B2 | 12/2015 | Sigg et al. | |
| 2001/0053873 A1 * | 12/2001 | Schaaf | A61F 9/00781 600/104 |
| 2003/0171722 A1 | 9/2003 | Paques et al. | |
| 2003/0211166 A1 | 11/2003 | Yamamoto et al. | |
| 2004/0054374 A1 | 3/2004 | Weber et al. | |
| 2004/0238781 A1 | 12/2004 | Landauer et al. | |
| 2004/0254154 A1 | 12/2004 | Ashton | |
| 2005/0009910 A1 | 1/2005 | Hughes et al. | |
| 2005/0015143 A1 * | 1/2005 | Willis | A61F 2/1608 623/6.36 |
| 2005/0029307 A1 * | 2/2005 | Py | A61F 9/0008 222/386 |
| 2005/0089545 A1 | 4/2005 | Kuwano et al. | |
| 2005/0165413 A1 | 7/2005 | Conston et al. | |
| 2005/0171507 A1 | 8/2005 | Christian et al. | |
| 2005/0244462 A1 | 11/2005 | Farooq | |
| 2006/0135973 A1 * | 6/2006 | Hawkins | A61B 17/3415 606/167 |
| 2006/0149194 A1 | 7/2006 | Conston et al. | |
| 2007/0063494 A1 | 3/2007 | Saito et al. | |
| 2007/0073275 A1 | 3/2007 | Conston et al. | |
| 2007/0202186 A1 | 8/2007 | Yamamoto et al. | |
| 2007/0233037 A1 | 10/2007 | Gifford et al. | |
| 2008/0033351 A1 | 2/2008 | Trogden et al. | |
| 2008/0058704 A1 | 3/2008 | Hee et al. | |
| 2008/0195135 A1 | 8/2008 | Attinger | |
| 2009/0043321 A1 | 2/2009 | Conston et al. | |
| 2009/0247955 A1 | 10/2009 | Yamamoto et al. | |
| 2010/0081707 A1 * | 4/2010 | Ali | A61F 9/0017 514/44 R |
| 2010/0173866 A1 | 7/2010 | Hee et al. | |
| 2010/0191176 A1 | 7/2010 | Ho et al. | |
| 2010/0191177 A1 | 7/2010 | Chang et al. | |
| 2010/0211079 A1 | 8/2010 | Aramant | |
| 2011/0071458 A1 * | 3/2011 | Rickard | A61F 9/00781 604/9 |
| 2011/0282270 A1 * | 11/2011 | Hall | A61B 17/00491 604/22 |
| 2012/0004595 A1 * | 1/2012 | Dubois | A61B 17/32002 604/22 |
| 2012/0022424 A1 | 1/2012 | Yamamoto et al. | |
| 2012/0048407 A1 | 3/2012 | Paden et al. | |
| 2012/0078224 A1 | 3/2012 | Lerner et al. | |
| 2012/0191064 A1 | 7/2012 | Conston et al. | |
| 2012/0226260 A1 | 9/2012 | Prausnitz et al. | |
| 2012/0232522 A1 | 9/2012 | Prausnitz et al. | |
| 2012/0271272 A1 * | 10/2012 | Hammack | A61F 9/0017 604/500 |
| 2012/0322144 A1 | 12/2012 | Lam et al. | |
| 2013/0149214 A1 | 6/2013 | Lam et al. | |
| 2013/0184631 A1 * | 7/2013 | Pinchuk | A61F 9/00781 604/8 |
| 2013/0216623 A1 | 8/2013 | Yamamoto et al. | |
| 2013/0245600 A1 | 9/2013 | Yamamoto et al. | |
| 2014/0025045 A1 | 1/2014 | Abt et al. | |
| 2014/0107566 A1 | 4/2014 | Prausnitz et al. | |
| 2015/0038905 A1 | 2/2015 | Andino et al. | |
| 2015/0148838 A1 | 5/2015 | Schaller | |
| 2015/0173947 A1 | 6/2015 | Charles | |
| 2015/0209180 A1 | 7/2015 | Prausnitz et al. | |

FOREIGN PATENT DOCUMENTS

| | | |
|---|---|---|
| AU | 2012200785 | 3/2012 |
| CN | 1348342 A | 5/2002 |
| CN | 102361605 A | 2/2012 |
| CN | 102458509 A | 5/2012 |
| CN | 103037802 A | 4/2013 |
| CN | 103327939 A | 9/2013 |
| EP | 1154691 A1 | 11/2001 |
| EP | 1178791 A2 | 2/2002 |
| EP | 2111821 A1 | 10/2009 |
| EP | 2468327 A1 | 6/2012 |
| EP | 2493368 A1 | 9/2012 |
| EP | 2563429 A2 | 3/2013 |
| EP | 2627292 A2 | 8/2013 |
| JP | 2001-525826 | 12/2001 |
| JP | 2012515627 A | 7/2012 |
| JP | 2012526637 A | 11/2012 |
| KR | 20040058309 | 7/2004 |
| KR | 10-20020080343 | 3/2010 |
| WO | WO 1992/08406 | 5/1992 |
| WO | WO 1994/12217 | 6/1994 |
| WO | WO 1995/017673 | 6/1995 |
| WO | WO 1996/009838 | 4/1996 |
| WO | WO 1998/051348 | 11/1998 |
| WO | WO 2002/058607 | 8/2002 |
| WO | WO2003045290 | 6/2003 |
| WO | WO 2004/027027 | 4/2004 |
| WO | WO 2004/073551 | 9/2004 |
| WO | WO 2005/069831 | 8/2005 |
| WO | WO 2005/107845 | 11/2005 |
| WO | WO 2006/042252 | 4/2006 |
| WO | WO 2007/047212 | 4/2007 |
| WO | WO 2007/100745 | 9/2007 |
| WO | WO 2007/131050 | 11/2007 |
| WO | 2009089409 A2 | 7/2009 |
| WO | WO 2010/132751 | 11/2010 |
| WO | WO 2011/057283 | 5/2011 |
| WO | WO2001041685 | 6/2011 |
| WO | WO 2011/106781 | 9/2011 |
| WO | WO 2011/139713 | 11/2011 |
| WO | WO 2012/012600 | 1/2012 |
| WO | WO 2012/051575 | 4/2012 |
| WO | WO 2012/106422 | 8/2012 |
| WO | WO 2014/036009 | 3/2014 |

(56) References Cited

FOREIGN PATENT DOCUMENTS

| WO | WO 2014/074823 | 5/2014 |
|---|---|---|
| WO | WO 2014/179698 | 11/2014 |
| WO | WO 2014/197317 | 12/2014 |

OTHER PUBLICATIONS

DORC Focus on Highlights Catalog, "Extendable 41G Subretinal injection Needle, 23 Gauge", Copyright 2012, p. 14.
Alcon Grieshaber Catalog, Copyright 2004, pp. 17-18.
Gizzard et al., "New Silicone Tipped Cannulas for Subretinal Fluid Drainage," British Journal of Ophthalmology, 1989,73, pp. 838-839.
MedOne Brochure, "Exactly What Your Looking For—High Quality Instruments for Vitreoretinal Surgery," 2012, 12 Pages.
Flynn et al. "Design Features and Surgical Use of a Cannulated Extrusion Needle," Graefe's Arch Clin Exp Ophthalmol 1989) 227:304-308, 5 pages.
Mcleod et al. "Modified Charles flute needle," British Journal of Ophthalmology, 1981, p. 69.
Patel, et. al. "Targeted Administration into the Suprachoroidal Space Using a Microneedle for Drug Delivery to the Posterior Segment of the Eye" Investigative Ophthalmology & Visual Science, Jul. 2012, vol. 53, No. 8., 9 pages.
Gilger, et. al. "Treatment of Acute Posterior Uveitis in a Porcine Model by Injection of Triamcinolone Acetonide Into the Suprachoroidal Space Using Microneedles" Investigative Ophthalmology & Visual Science, Apr. 2013, vol. 54, No. 4, 10 pages.
Peyman, et al. "Delivery systems for intraocular routes"; Advanced Drug Delivery Reviews 16 (1995), pp. 107-123.
Olsen, et al. "Cannulation of the Suprachoroidal Space: A Novel Drug Delivery Methodology to the Posterior Segment" American Journal of Ophthalmology, Nov. 2006, vol. 142, No. 5, pp. 778-787.e2.
Silva, et al. "Trans-scleral delivery of polyamine analogs for ocular neovascularization" Experimental Eye Research 83 (2006), pp. 1260-1267.
Weijtens, et al. "Dexamethasone Concentration in the Subretinal Fluid after a Subconjunctival Injection, a Peribulbar Injection, or an Oral Dose" Ophthalmology vol. 107, No. 10, Oct. 2000, pp. 1932-1938.
Patel, et al. "Targeted Drug Delivery to the Eye Enabled by Microneedles" Chapter 14, U.B. Kompella and H.F. Edelhauser (eds.), Drug Product Development for the Back of the Eye, 331 AAPS Advances in the Pharmaceutical Sciences Series 2, 2011, pp. 331-360.
Jiang, et al. "Intrascleral Drug Delivery to the Eye Using Hollow Microneedles" Pharmaceutical Research, vol. 26, No. 2, Feb. 2009, pp. 395-403.
Patel, et al. "Suprachoroidal Drug Delivery to the Back of the Eye Using Hollow Microneedles" Pharm Res (2011) 28:166-176.
Ambati, et al. "Transscleral Delivery of Bioactive Protein to the Choroid and Retina" Investigative Ophthalmology & Visual Science, Apr. 2000, vol. 41, No. 5, pp. 1186-1191.
Jiang, et al. "Coated Microneedles for Drug Delivery to the Eye" Investigative Ophthalmology & Visual Science, Sep. 2007, vol. 48, No. 9, pp. 4038-4043.
Krohn, et al. "Light microscopy of uveoscleral drainage routes after gelatin injections into the suprachoroidal space" Acta Ophthalmol. Scand. 1998: 76:521-527.
Lee, et al. "Drug delivery through the sclera: effects of thickness, hydration, and sustained release systems" Experimental Eye Research 78 (2004), pp. 599-607.
International Search Report and Written Opinion issued for PCT/US2014/064407, dated Apr. 8, 2015, 13 pgs.

\* cited by examiner

SYSTEMS AND METHODS FOR SUBRETINAL DELIVERY OF THERAPEUTIC AGENTS

BACKGROUND

The present disclosure relates to systems and methods for use during surgical procedures, and more particularly, to the delivery of therapeutic agents into subretinal space during an ophthalmic surgical procedure.

Medical researchers are pioneering various treatments for diseases and conditions. Some conditions are pathogenic while others are congenital. The advancing knowledge of genetic therapies is providing hope for those suffering from a wide range of such conditions, including ophthalmic conditions. In seeking to treat certain eye problems, genes or stem cells may be injected through a fine needle inserted through the eye cavity and under the retina. A small perforation is made in the retina to access the subretinal space. A surgeon maintains the needle in place while another surgeon or assistant injects a fluid containing therapeutic agents through the needle.

Thus, some operations currently require two surgeons to control the puncturing and the injection of fluid containing therapeutic agents. Positioning the needle in the retina depends entirely on the surgeon's observation and experience. Additionally, reflux of fluid back into the eye cavity through the puncture site makes it difficult to apply a consistent, desired volume of the therapeutic agent.

Therefore, there remains a need for improved systems and methods for subretinal delivery of therapeutic agents. The present disclosure is directed to addressing one or more of the deficiencies in the prior art.

SUMMARY

In one exemplary aspect, the present disclosure is directed to a retinal treatment device for delivering therapeutic agents to a target location within a retina. The retinal treatment device includes an outer tube having a lumen and having a distal end and a proximal end, the outer tube being sized to penetrate an eye to conduct retinal surgeries. The retinal treatment device further includes a flexible tip affixed to the distal end of the outer tube. The flexible tip is configured to flexibly conform to a retinal surface when abutted against the retinal surface. The retinal treatment device also includes an inner tube disposed within the lumen of the outer tube, the inner tube having a proximal end and a distal end. The distal end of the inner tube extends into the flexible tip, the inner tube configured to extend from the flexible tip and penetrate an inner limiting membrane of the retina. A chamber is coupled to the proximal end of the inner tube. The chamber is configured to receive a fluid containing therapeutic agents injectable through the inner tube beyond the inner limiting membrane of the retina when the inner tube penetrates the inner limiting membrane of the retina.

In another exemplary aspect, the present disclosure is directed to a retinal treatment system for delivering therapeutic agents to a target location with a retina. The retinal treatment system includes a console having a control system and a handheld device coupled to the control system by a communication line. The handheld device includes an inner tube disposed within an outer tube and being axially moveable within the outer tube. The inner tube has a perforating tip at a distal end thereof that is configured to perforate an inner limiting membrane of the retina. The handheld device further includes a chamber coupled to a proximal end of the inner tube. The chamber is configured to receive a fluid containing therapeutic agents injectable from the perforating tip. The control system of the retinal treatment system permits a user to maintain a position of the handheld device relative to the retina and activate an injection of a portion of the fluid through the inner tube into the retina.

In yet another exemplary aspect, the present disclosure is directed to a method of delivering therapeutic agents into a retina of an eye a patient. The method includes steps of penetrating a vitreous chamber of the eye with a retinal treatment device and of positioning the retinal treatment device in contact with the retina so as to form a seal by sealing means between the retinal treatment device and the retina. The method further includes a step of activating an injection routine that forms a bleb containing therapeutic agents in the retina and a step of withdrawing the retinal treatment device from the vitreous chamber.

It is to be understood that both the foregoing general description and the following drawings and detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following.

BRIEF DESCRIPTION OF THE DRAWINGS

The accompanying drawings illustrate embodiments of the devices and methods disclosed herein and together with the description, serve to explain the principles of the present disclosure.

These figures are better understood by reference to the following detailed description.

DETAILED DESCRIPTION

For the purposes of promoting an understanding of the principles of the present disclosure, reference will now be made to the embodiments illustrated in the drawings and specific language will be used to describe them. It will nevertheless be understood that no limitation of the scope of the present disclosure is intended. Any alterations and further modifications to the described devices, instruments, methods, and any further application of the principles of the present disclosure are fully contemplated as would normally occur to one skilled in the art to which the present disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

The present disclosure relates generally to systems, delivery devices, and methods of delivering therapeutic agents into the subretinal area of a patient's eye. In some aspects, a delivery device ensures a roughly fixed depth of penetration by a needle into the subretinal space and provides a seal at the puncture site to prevent reflux of the fluid containing therapeutic agents, such as genes or stem cells, back into the eye cavity. In some aspects, the system permits the activation of an injection routine by a surgeon, while the surgeon maintains a tip of the delivery device within the retina of a patient. Thus, using the delivery device, a single surgeon may apply a treatment to a patient in a more controlled manner.

Figure 1:
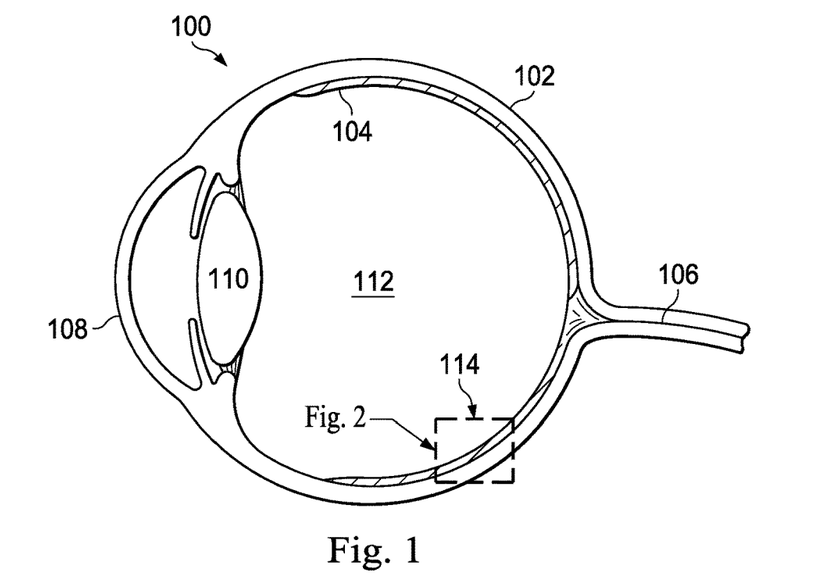
FIG. 1 is a cross-sectional illustration of an eye of a patient.

FIG. 1 is a cross-sectional illustration of an eye 100. A number of features of the eye 100 are illustrated herein. The eye 100 includes a sclera 102 that is coupled to a retinal membrane or retina 104 by a choroid (not illustrated in FIG. 1). The choroid includes connective tissue to attach the retina 104 to the inside wall of the sclera 102 at the back of the eye 100 and to provide oxygen and nourishment to the outer layers of the retina 104. A cornea 108 permits light to enter the eye 100, the light being focused by a lens 110 through a vitreous chamber 112 onto the retina 104, which contains photo-activated cells that transmit signals over the optic nerve 106 to the brain.

Problems may develop in the eye that prevent the proper development and/or function of the retina as it provides signals to the brain for processing into cognizable images. A potential treatment or therapy for such eye problems including delivering genetic material and/or stem cells into a desired region of the subretinal space, the area between the outermost surface of the retina and the retinal pigment epithelium (RPE), just above the choroid, where the immune response may be sufficiently subdued.

An area of interest 114 is shown in FIG. 1 on a lower portion of the eye 100. The area of interest 114 is shown in more detail in FIG. 2.

Figure 2:
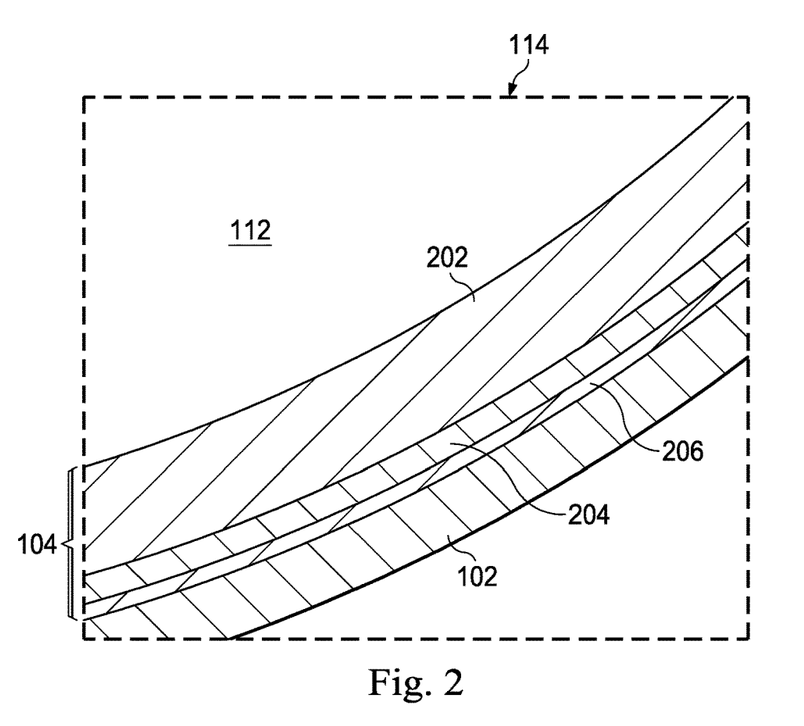
FIG. 2 is a cross-sectional illustration of a portion of the retina of the eye shown in FIG. 1.

Referring now to FIG. 2, the area of interest 114 of the eye 100 is shown in close-up to provide greater, schematic detail of the layers of the retina 104. The layers are not drawn to scale. As shown in FIG. 2, the retina 104 includes several layers, including a main retinal layer 202, a sub-retinal space 204, and an opaque layer 206. The retinal layer 202 includes an inner limiting membrane that is in contact with the vitreous humor that fills the vitreous chamber 112. The retinal layer 202 further includes a nerve fiber sub-layer, a ganglion cell sub-layer, an inner plexiform sub-layer, an inner nuclear sub-layer, an outer plexiform sub-layer, and an outer nuclear sub-layer. The retinal layer 202 also includes an external limiting membrane and a photoreceptor sub-layer. The opaque layer 206 includes the retinal pigment epithelium (RPE) and the choroid.

When therapeutic agents are delivered to the retina 104, the fluid containing the therapeutic agents is delivered between the retinal layer 202 and the retinal pigment epithelium of the opaque layer 206, i.e., in the subretinal space 204. A fine needle is used to puncture the retinal layer 202 to allow the fluid containing the therapeutic agents into this subretinal space. A bleb is formed by the injection of a balanced salt solution (BSS), then a fluid containing therapeutic agents is injected into the space formed by the bleb. The formation of the bleb provides the space in which to inject the therapeutic agents without subject them to the fluid pressures necessary to form that space. In some embodiments, a single injection may be used to form the bleb and introduce the therapeutic agents. The fluid containing the therapeutic agents is introduced into the subretinal space 204 between the photo-receptor sub-layer and the retinal pigment epithelium, where immune system reactions to the therapeutic agents may be relatively subdued.

Care must be taken to avoid puncturing the retinal pigment epithelium of the opaque layer 206 in the process. Because the retina 104 is often less than about 0.5 millimeters thick, ensuring the proper penetration depth may be difficult. Additionally, the volume of fluid containing the therapeutic agents is injected into the subretinal space 204, back flow or reflux of the therapeutic agents from the bleb back through the puncture in the retinal layer 202 into the vitreous chamber 112 can potentially result in the formation of tumors from misplaced stem cells or in the loss of therapeutic agents, which may decrease the efficacy of treatment. Thus, the total volume of fluid injected should be controlled.

The systems, devices, and methods of this disclosure, embodiments of which are described herein, may facilitate the proper positioning of the perforating tip of the fine needle in the retina 104, may prevent reflux into the vitreous chamber, and may enable a single surgeon to perform the operation.

Figure 3:
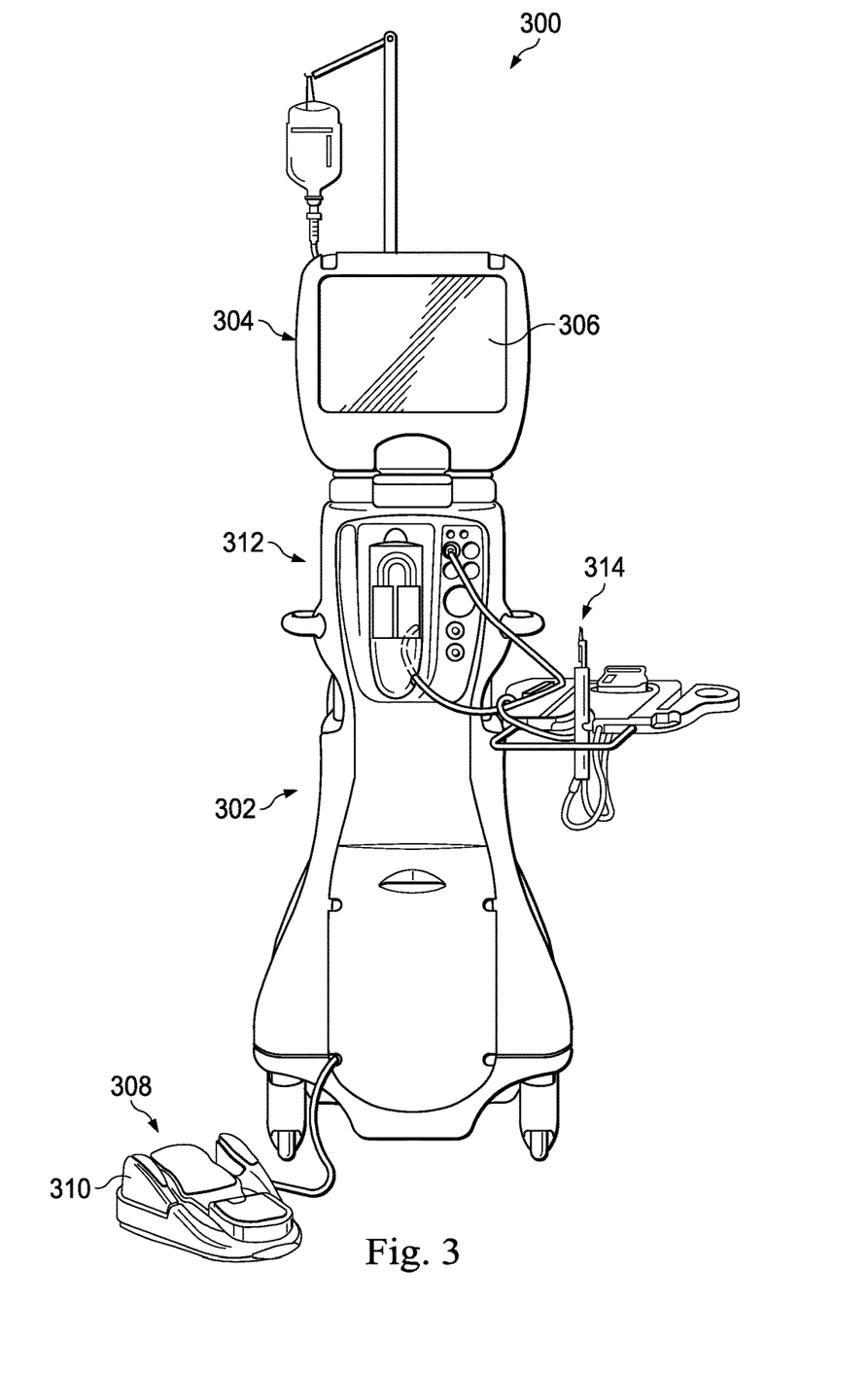
FIG. 3 is an illustration of a retinal treatment system according to exemplary aspects of the present disclosure.

FIG. 3 illustrates an exemplary retinal treatment system, generally designated as console 300. The console 300 includes a base housing 302 with a computer unit 304 and an associated display screen 306 adapted to show data relating to system operation and performance during ophthalmic surgical procedures. The console 300 also includes a number of subsystems that may be used together to perform a vitrectomy surgical procedure prior to the injection of therapeutic agents in order to provide improved access to the retina. For example, the subsystems include a control system that has one or more of a foot pedal subsystem 308 including a foot pedal 310 having a number of foot actuated controls and a device control system or subsystem 312 in communication with a hand-held surgical instrument shown as delivery device 314. Another subsystem may be used to provide tracking of a distal end of the delivery device 314. This may be done using optical coherence tomography (OCT), by using a displacement sensor, or by other appropriate mechanisms. The tracking information and other information may be provided to the display screen 306 or to a surgical microscope heads-up display. Some embodiments of the console 300 may further include a vitrectomy cutter subsystem with a vitrectomy hand piece that can also be controlled using the foot pedal 310 and the device control subsystem 312. These subsystems of console 300 may overlap and cooperate to perform various aspects of a procedure and may be operable separately and/or independently from each other during one or more procedures. That is, some procedures may utilize one or more subsystems while not using others.

Figure 4:
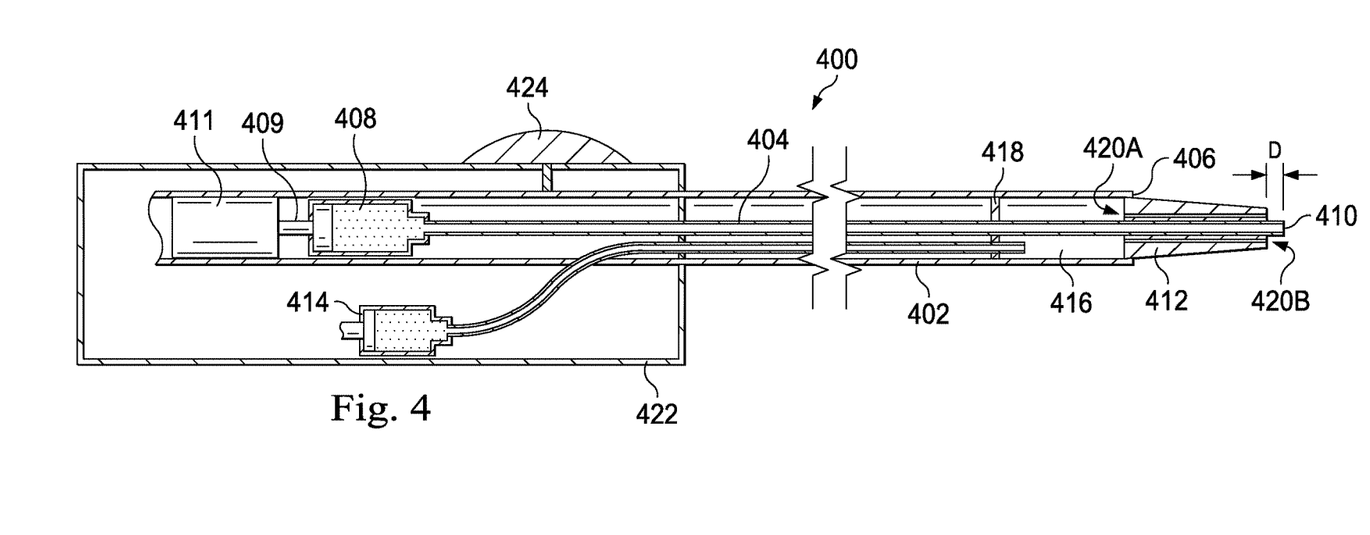
FIG. 4 is a cross-sectional illustration of a subretinal delivery device according to exemplary aspects of the present disclosure.

Referring now to FIG. 4, a subretinal delivery device 400 is illustrated in cross-section. The delivery device 400 may be used as the delivery device 314 of the console 300 of FIG. 3. The delivery device 400 includes an outer tube 402 and an inner tube or needle 404. In exemplary some embodiments, the outer tube 402 is a 23 or 25 gauge needle, while the needle 404 is a finer gauge needle, such as a 38 gauge needle. Other sizes of outer tubes and needles may be used in other embodiments. The needle 404 is positioned within the outer tube 402 and extends beyond a distal end 406 thereof.

A proximal end of the needle 404 is coupled to an actuatable chamber 408 which contains therapeutic agents, such as, for example, genes, stem cells, or other agents suspended in a fluid. When the chamber 408 is activated, a plunger 409 forces some or all of the fluid through the needle 404 and out a perforating distal tip 410 thereof. The plunger 409 of the chamber 408 may be activated mechanically, electrically, and/or pneumatically, under the control of the device control subsystem 312 of the console 300 of FIG. 3. The control subsystem 312 may communicate by a communication line to an actuator 411 that is coupled to drive the plunger 409. In some embodiments, a pre-packaged cartridge of fluid containing therapeutic agents is provided for insertion into the chamber 408. The plunger 409 may engage with the cartridge, in such embodiments, to controllable eject the contents through the needle 404. In some embodiments, the subretinal delivery device includes a first chamber that contains a balanced salt solution for the formation of the bleb and a second chamber for the fluid containing the therapeutic agents, with both chambers being coupled to the needle 404. Additionally, some embodiments of the pre-packaged cartridge may include a first portion containing the balanced salt solution, configured to be injected first, and a second portion containing the therapeutic agents, configured to be injected after the first portion.

In the illustrated embodiment of the subretinal delivery device 400, a tip structure 412 is sealingly coupled to the distal end 406 of the outer tube 402. The tip structure 412 is coupled to the outer tube 402 such that any fluid in the central lumen of the outer tube 402 does not leak out. A distance D is labeled in FIG. 4 between the perforating distal tip 410 of the needle 404 and a distal end of the tip structure 412. This distance D may be a desired penetration depth at which therapeutic agents are to be delivered into the subretinal space 204, and thus may be approximately the distance through the retinal layer 202. Distance D may range from about 100 to about 350 microns or more. In some embodiments, the distance D is controlled by the console 300 and can be adjusted by a surgeon using an interface provided thereby. In some instances, a surgeon may determine the thickness of the retinal layer 202 using optical coherence tomography or another technique before using the interface to select the appropriate distance D. The console 300 communicates with the subretinal delivery device 400 to move the needle 404 as needed. While the perforating distal tip 410 is sharpened for penetration through the retinal layer 202 of the eye 100, the broader surface area of the distal end of the tip structure 412 may act to inhibit further penetration of the delivery device 400 into the subretinal space, preventing a surgeon from puncturing the RPE and missing the subretinal space.

The illustrated embodiment of the delivery device 400 also includes a sealing gel chamber 414. Like the chamber 408, the sealing gel chamber 414 may be actuated mechanically, electrically, or pneumatically by the plunger 409 controlled by the control system of console 300 of FIG. 3. Unlike the chamber 408, the sealing gel chamber 414 contains a tissue sealant or sealing gel instead of therapeutic agents. The chamber 414 is actuated to expel the sealing gel into a chamber 416 formed by the outer tube 402, the tip structure 412, and a barrier wall 418. As illustrated, the sealing gel is a hydrogel that is cohesive and adheres to the tissue of the retina. Once the chamber 416 is filled, additional sealing gel introduced from the chamber 414 is force out of one or more openings through the distal end 406 of the outer tube. In the illustrated embodiment featuring the tip structure 412, two such openings are depicted: opening 420A and opening 420B. Some embodiments may include an annular opening or more include more than three openings.

Either before or during contact between the distal end of the tip structure 412 and the limiting membrane of the retinal layer 202, a volume of sealing gel is expelled from the sealing gel chamber 414 into contact with the retinal layer 202. The sealing gel provides or enhances a seal between the delivery device 400 and the retina 104 such that when the chamber 408 is actuated, to form a bleb and/or to inject the therapeutic agents, reflux of the therapeutic agents into the vitreous chamber 112 is inhibited or eliminated.

As illustrated in FIG. 4, both of the chambers 408 and 414 are included in a housing 422. The housing 422 may be shaped and sized to fit in the hand of a surgeon performing the retinal treatment. Although the chamber 408 is illustrated as positioned within the outer tube 402, in some embodiments the chamber 408 may be situated elsewhere in the housing 422.

By using the console 300 of FIG. 3, including the footswitch 308, a single surgeon may position the delivery device 400 such that the distal tip 410 of the needle 404 is positioned desirably in the subretinal space and, while maintaining the positioning of the delivery device 400, trigger the actuation of the therapeutic fluid chamber 408 and the sealing gel chamber 414 to inject the controlled, predetermined volume of fluid containing therapeutic agents and to prevent reflux of those agents.

In some embodiments, the delivery device 400 further includes a knob 424 configured on the housing 422 of the delivery device 400. The knob 424 may be a slider or a wheel-type knob that is mechanically coupled to the inner tube 404, such that by manipulating the knob 424, the inner tube 404 may be moved relative to the outer tube 402. For example, in some embodiments, the inner tube 404 may be advanced relative to the outer tube 402 and into a subretinal space, through the retinal layer 202. In some additional embodiments, the knob 424 may provide for a plurality of detent positions, such that when the knob is moved from one detent position to another, the inner tube 404 is moved relative to the outer tube by a known distance, such as by 25 microns. Thus, a desired distance D can be selected by moving the knob 424 an appropriate number of detent positions.

Figure 5A:
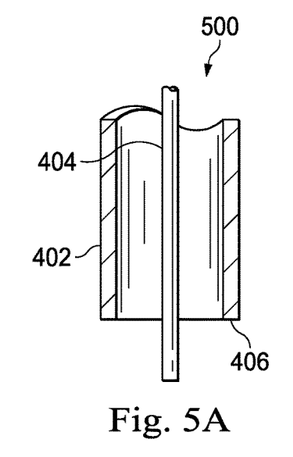
FIGS. 5A, 5B, 5C, 5D, 5E, and 5F are cross-sectional illustrations of distal ends of subretinal delivery devices according to exemplary aspects of the present disclosure.
Figure 5B:
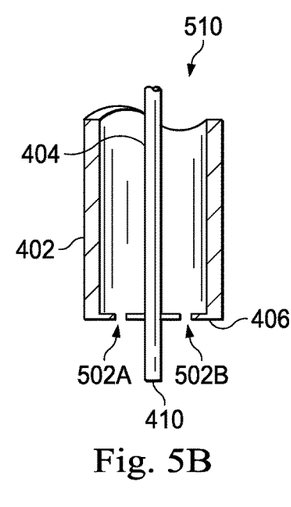
Figure 5C:
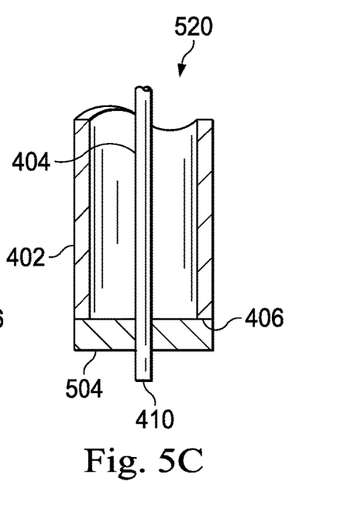

FIGS. 5A-F illustrate a plurality of embodiments of the distal end of the delivery device 400. FIG. 5A illustrates the outer tube 402 having an abrupt distal end 406 that abuts the needle 404, which protrudes beyond the distal end 406 by a distance D as seen in FIG. 4. FIG. 5B illustrates a distal end 510 that is similar to the distal end 500 of FIG. 5A. The distal end 510 further includes two openings 502A and 502B. Other embodiments may include more or fewer openings. The openings 502A and 502B permit a tissue sealant or sealing gel to be expelled from the lumen of the outer tube 402 toward the tip of the needle 404, thereby providing or improving a seal at the puncture site. FIG. 5C illustrates a distal end 520. The distal end 520 shares many of the features illustrated in the distal end 500 of FIG. 1A, but further includes a soft cap 504 affixed to the distal end 406 of the inner tube 402. The soft cap 504 may be made from a plastic or polymer material such as silicone, and may provide a seal when engaged with or compressed against the retina 104, conforming thereto, thereby preventing reflux.

Figure 5D:
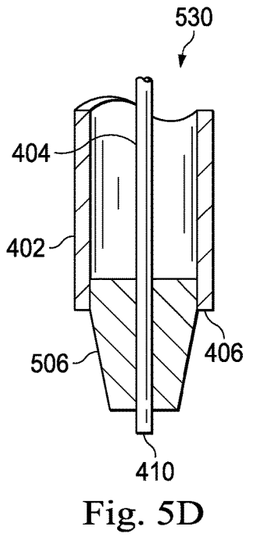
Figure 5E:
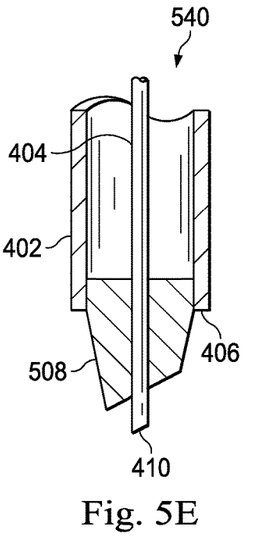
Figure 5F:
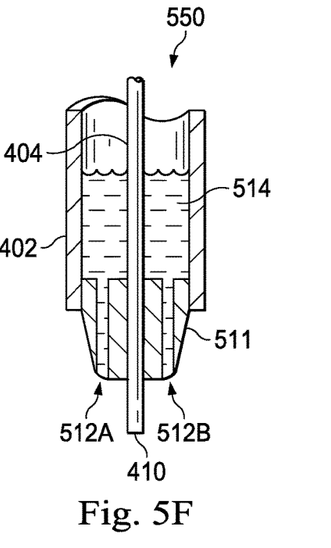

FIGS. 5D-F are also cross-sectional illustrations of embodiments of distal ends of a delivery device 400. FIG. 5D illustrates a distal end 530 that has a frustoconical tip structure 506 extending from about the distal end 406 of the outer tube 402. The tip structure 506 may be formed from a soft material that deforms somewhat when compressed against the retina 104 of the eye 100. The distal end 540 illustrated in FIG. 5E is similar to that of FIG. 5D, but the distal end of the tip structure 508 has a terminal surface that is slanted such that it is not orthogonal to the needle 404 running therethrough. Similarly, the tip 410 of the needle 404 is slanted. This may decrease an amount of force necessary to puncture the retinal layer 202 of the retina 104. FIG. 5F illustrates a distal end 550 of a delivery device 400. The distal end 550 includes a tip structure 511, which is similar to the tip structure 506 of FIG. 5D. However, the tip structure 511 includes two illustrated openings 512A and 512B, through which a sealing gel 514 may be injected to form a seal or enhance the seal formed by the tip structure 511 flexing to conform to the surface of the retina 104. The various features of the distal ends of the delivery device 400, as illustrated in FIGS. 5A-F, may be combined in additional embodiments.

Figure 6A:
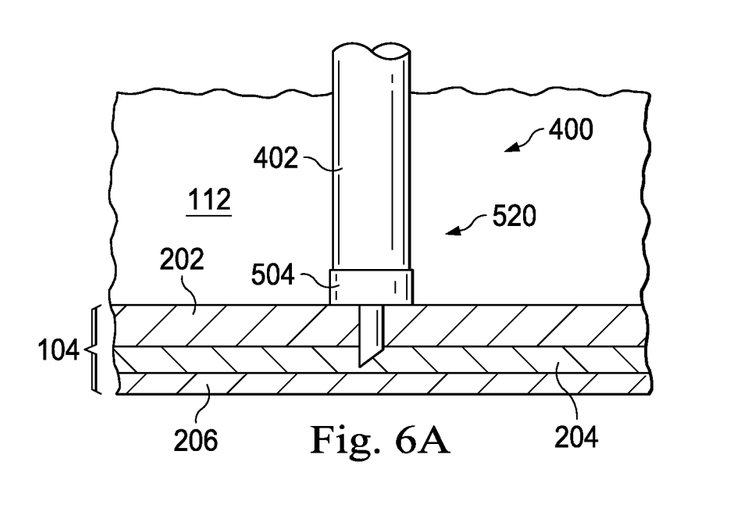
FIGS. 6A and 6B are lateral views of alternative embodiments of a subretinal delivery device providing a seal at a retinal surface according to exemplary aspects of the present disclosure.
Figure 6B:
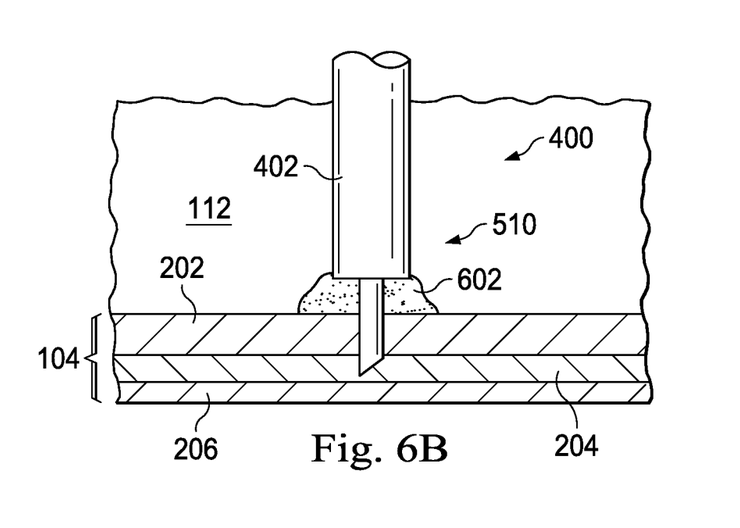

Referring now to FIGS. 6A and 6B, which are side-view illustrations of embodiments of the delivery device 400 of FIG. 4. The distal end of the delivery device 400 shown in FIG. 6A is similar to the distal end 520 of FIG. 5C, although as seen in FIG. 6A, the needle 404 has an angled tip 410. FIG. 6A illustrates the delivery device 400 as inserted into a retina 104 as depicted in FIG. 2. As illustrated, the needle 404 extends beyond a soft cap 504 positioned at the distal end of the outer tube 402. The needle 404 extends a distance such that the tip 410 is in the subretinal space 204. By holding the delivery device in contact with the surface of the retina 104 and applying slight pressure, the soft cap 504 conformingly compresses against the surface of the retina 104 to form a seal. The seal prevents back flow or reflux of injected fluid containing therapeutic agents, thereby preventing the therapeutic agents from entering the vitreous chamber 112.

FIG. 6B illustrates another mechanism for providing a seal to prevent reflux. The distal end 406 of the delivery device 400 in FIG. 6B is a distal end 510 illustrated in FIG. 5B and described herein. The distal end includes one or more holes such that a sealing gel 602 may be expelled therefrom to provide the seal. In some embodiments, the sealing gel 602 is a predetermined volume of sealing gel expelled from the delivery device 400 in a controlled manner after being triggered by the surgeon. The sealing gel 602 may be expelled prior to contact between the outer tube 402 and the surface of the retina 104. The soft cap 504 and the sealing gel 602 may both serve to provide a predictable separation distance between the distal end of the outer tube 402 and the distal tip 410 of the needle 404. For example, the separation distance may be about 250 microns or more such that when the therapeutic agents are injected into the subretinal space 204, they are injected in the optimal location.

Figure 7A:
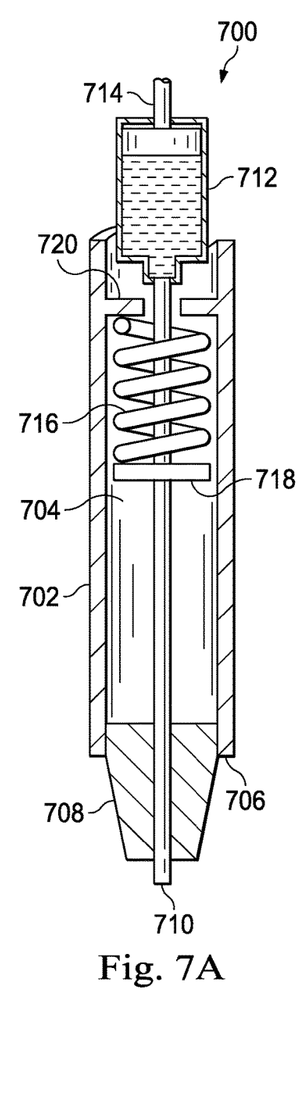
FIGS. 7A, 7B, and 7C are cross-sectional illustrations of subretinal delivery devices showing pressure-moderation mechanisms according to exemplary aspects of the present disclosure.
Figure 7B:
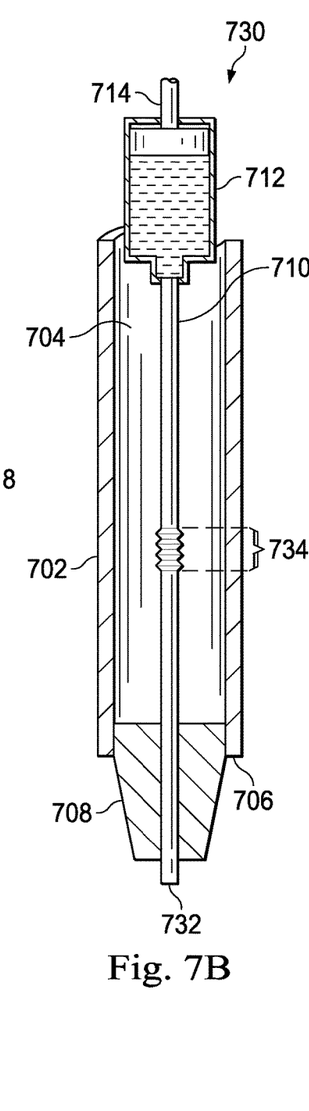
Figure 7C:
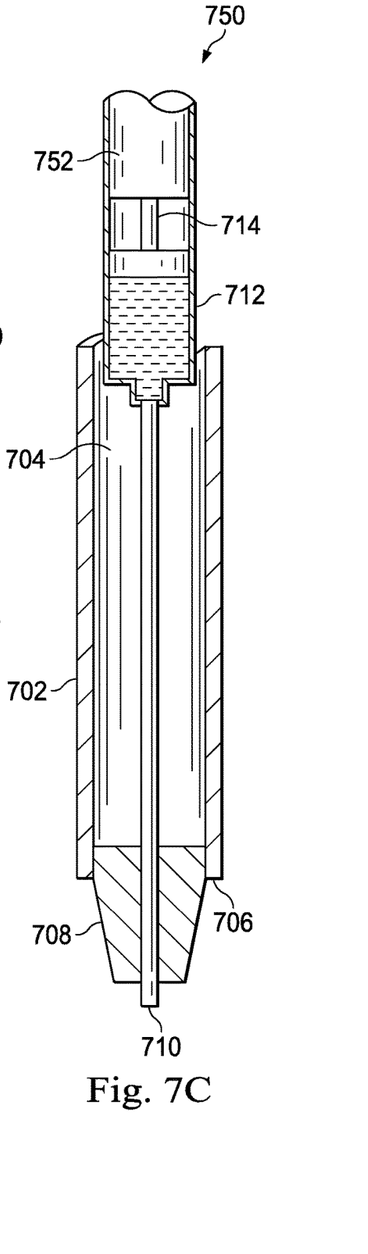

Referring now to FIGS. 7A, 7B, and 7C, these figures illustrate embodiments of a subretinal therapeutic agent delivery device have a force moderation structure. In FIG. 7A, a portion of delivery device 700 is depicted in cross-section. The delivery device 700 includes an outer tube 702 having a lumen 704 therein. A distal end 706 of the outer tube 702 includes a tip structure 708 affixed therein. Through a hole in the center of the tip structure 708 runs a needle 710 extending a distance there from. The needle 710 extends through the lumen 704 to a chamber 712 which contains therapeutic agents suspended in a fluid. A plunger 714 is coupled to the chamber 712 to eject the volume of fluid from the chamber 712 when subjected to an activation or actuation energy. As illustrated, the lumen 704 further includes a spring or biasing element 716. As illustrated, the biasing element 716 is coupled to the needle 710 by a coupling member 718 on one side and contacts a ring 720 that protrudes inwardly from the inner surface of the outer tube 702. By selecting an appropriate spring constant of the biasing element 716, a force applied by the needle 710 on the components of a retina may be limited so as to prevent a surgeon from puncturing the retinal pigment epithelium while permitting the surgeon to puncture the limiting membrane of the retina, thereby accessing the subretinal space. The force required to puncture the RPE is greater than the force required to puncture the limiting membrane. In this way, the biasing element 716 serves as a force moderation structure. Then, by actuating the chamber 710 with the plunger 714, the desired volume of fluid containing therapeutic agents may be injected into the subretinal space.

FIG. 7B is a cross-sectional illustration of a delivery device 730, which shares a number of features in common with a delivery device 700 as described herein, but includes a different force moderation structure. As illustrated in FIG. 7B, the delivery device 700 includes an outer tube 702 having a lumen 704 therein. A distal end 706 of the outer tube 704 is coupled to a tip structure 708. The needle 732 is inserted through the lumen 704 and through the tip structure 708 such that the needle 732 may be moved along the axis of the outer tube 702. Unlike the delivery device 700 which included a spring 716 as a biasing element, the needle 732 provides a spring constant by including a biasing element that is a corrugated section 734, having an accordion-like cross-section. The corrugated section 734 of the needle 732 allows the needle 732 to compress when subjected to a certain degree of force. For example, the corrugated section 734 may compress when the needle 732 is pushed against the retinal pigment epithelium, thereby preventing the needle 732 from puncturing the RPE. Thereby, the corrugated section 734 may provide a force moderation structure.

FIG. 7C is a cross-sectional illustration of a delivery device 750 that shares many of the features of the delivery devices 730 and 700, but includes a different force moderation structure. In the delivery device 750 the chamber 712 and the plunger 714 are positioned within a rigid coupler 752. The rigid coupler 752 contains the chamber 712 and rigidly couples the chamber 712 to the needle 710. The rigid coupler 752 may be coupled to an actuator, such as a mechanical or pneumatic actuator, that may rapidly move the needle 710 forward a predetermined distance, with the plunger 714 able to move independently of the rigid coupler 752 as provided by an actuator 715. For example, when the delivery device 750 is brought into contact with the retina by a surgeon, a tip of the needle 710 may be positioned within the tip structure 708. By triggering the actuator 715, such as by tapping a switch on a foot pedal or otherwise using a control system, the surgeon may cause the rigid coupling 752 and the needle 710 to be forced forward a predetermined distance greater than the thickness of the retinal layer 202 but less than the distance from the inner surface of the limiting membrane to the RPE. Thus, the mechanical or pneumatic actuator coupled to the rigid coupler 752 may position the tip of the needle 710 desirably within the subretinal space.

Figure 8A:
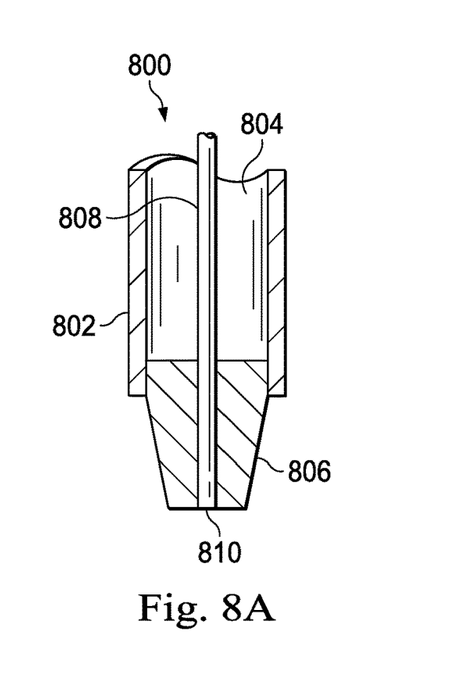
FIGS. 8A and 8B are cross-sectional illustrations of a subretinal delivery device with a delivery needle in two states according to exemplary aspects of the present disclosure.
Figure 8B:
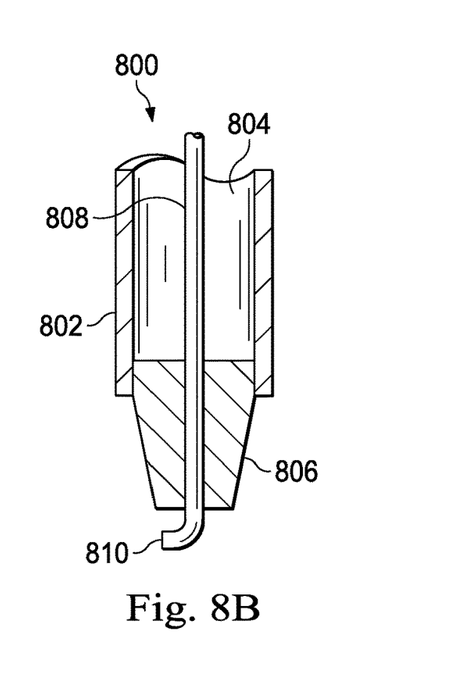

FIGS. 8A and 8B are cross-sectional illustrations of a distal end of a delivery device 800, similar in appearance to that shown in FIG. 4. FIG. 8A illustrates the delivery device 800 in a retracted state, while FIG. 8B illustrates the delivery device 800 in an extended state. The delivery device 800 includes an outer tube 802 having a lumen 804 extending therethrough. A distal end of the outer tube 802 is coupled to a tip structure 806 that has a needle 808 moveably inserted therein. The needle 808 is formed from a memory material that causes the needle 808 to be curved in a natural state. While the tip 810 of the needle 808 is positioned within the tip structure 806, the tip 810 remains substantially straight as illustrated in FIG. 8A. When the tip 810 of the needle 808 is extended beyond the tip structure 806, the natural shape of the memory material of the needle 808 becomes apparent as seen in FIG. 8B. As illustrated, the tip 810 in a natural state may have a radius of curvature ranging from about 100 microns to about 350 microns or more. Other embodiments of the tip 810 of the needle 808 of the delivery device 800 may have a larger or smaller radius of curvature. Embodiments of delivery devices having needles that curve when extended beyond a tip structure may avoid puncturing the retinal pigment epithelium by preventing any contact between a tip of the needle and RPE. In some embodiments, the memory material is a shape memory alloy, a polymer, or other material.

By controlling the depth and angle of entry of the fluid containing therapeutic agents into the subretinal space, the stresses applied to the therapeutic agents may be decreased. When therapeutic agents flow from a chamber through a needle, out of a tip thereof, and into the layers of the subretinal space, the therapeutic agents are exposed to sheering stresses that may damage them, decreasing the efficacy of treatment. The sheering stresses may be mitigated by shaping the tip of the injecting needle. For example, the curved tip 810 as the delivery device 800 may lower the sheering stresses. Also, having a beveled or angled tip of the injecting needle may decrease the sheering stresses. In order to decrease the stresses experienced while flowing through the injecting needle, the inside surface of the needle may be treated to decrease friction. For example, the injecting needles as disclosed herein in delivery devices 400, 800, and others, may have their inside surfaces coated with Teflon® or a similar friction-reducing coating. The tip of injecting needles may also impact the distribution of therapeutic agents into the subretinal space providing a bleb with a larger or smaller footprint.

Figure 9:
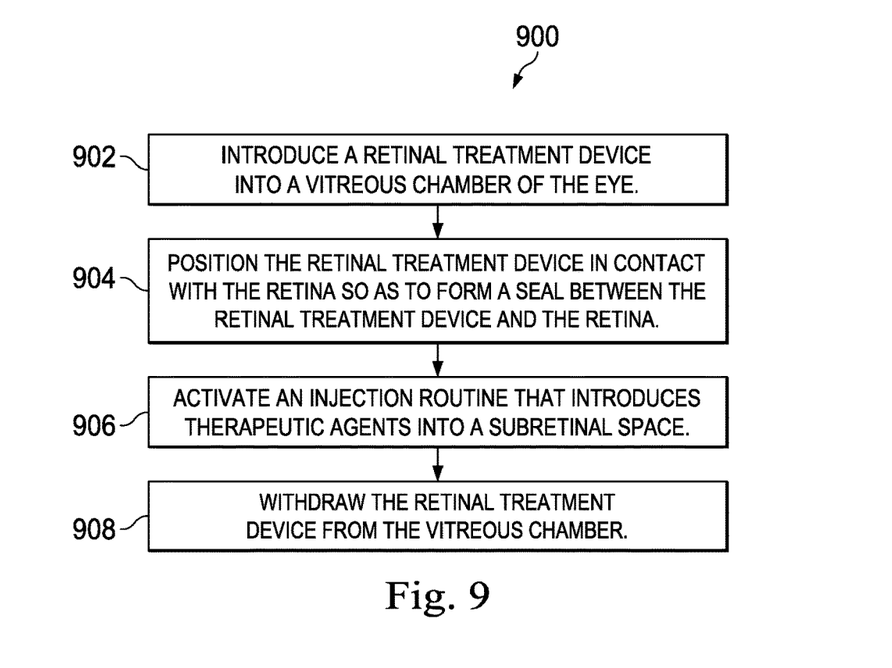
FIG. 9 is a flowchart of a method of delivering therapeutic agents into a retina of an eye of a patient according to exemplary aspects of the present disclosure.

FIG. 9 is a flowchart of a method 900 of delivering therapeutic agents into a retina of an eye a patient. As illustrated in FIG. 9, the method 900 includes several enumerated steps. However, embodiments of method 900 may include additional steps before, after, in between, and/or as part of the enumerated steps. Thus, method 900 may begin in step 902 in which a surgeon introduces a retinal treatment device into a vitreous chamber of the eye. The retinal treatment device may be a delivery device like the delivery device 400 of FIG. 4, or another delivery device described herein, and may be part of a retinal treatment system like the console 300 illustrated in FIG. 3. The surgeon may insert the delivery device 400 through the sclera of the eye into the vitreous chamber. Additional procedures, such as a vitrectomy procedure may be performed earlier.

In step 904, the surgeon positions the retinal treatment device in contact with the retina so as to form a seal between the retinal treatment device and the retina. This may be accomplished in several ways. As illustrated in FIG. 6A, a soft cap may be coupled to the distal end of the outer tube of a delivery device after the needle of the retinal treatment device punctures the limiting membrane of the retina. By applying slight pressure with the delivery device, the surgeon causes the soft cap to conform to the upper surface of the retina, thereby forming a seal. In some embodiments of the method 900, the surgeon forms the seal between the retinal treatment device and the retina by expelling a tissue sealant or sealing gel from the distal end of the delivery device. The sealing gel forms a seal between the retina and the retinal treatment device, preventing reflex of the fluid containing the therapeutic agents back into the vitreous chamber. Combinations of these sealing techniques may be employed by the surgeon in some embodiments.

In step 906, an injection routine is activated to introduce therapeutic agents into a subretinal space. The surgeon may trigger the injection routine by using the foot pedal 310 of the foot pedal subsystem 308 coupled to the console 300. The foot pedal 310 sends a signal to the console 300, which is interpreted by the console as an instruction to activate an actuator, such as the actuator 408 of the delivery device 400. Thus, the console 300 may control the injection of therapeutic agents by controlling the actuator 408. The injection routine may control a flow rate in addition to a volume of fluid and/or a sheer stress applied to the therapeutic agents. The console 300 may provide for the selection of predetermined values using an interface. The injection routine may also control an injection pressure. Additionally, embodiments of the injection routine as included in method 900 may activate a needle penetration action. For example, the console 300 may instruct the actuator 752 of the delivery device 750 as illustrated in FIG. 7C. Alternatively, the housing 422 may include a knob for inserting the needle in a controlled manner. The knob may be a continuous or stepped knob, in which case each step may move the needle a constant amount, such as 10 or 25 microns. The injection routine may include an initial step of forming a bleb with fluid not containing therapeutic agents, such as a balanced salt solution or saline solution, prior to injecting the therapeutic agents. For example 100 microliters of the balanced salt solution may be injected to form the bleb. This may provide improved dispersion of the therapeutic agents and may prevent damage to the therapeutic agents from the higher pressures associated with bleb formation.

In step 908, the surgeon withdraws the retinal treatment device from the vitreous chamber. In embodiments in which a sealing gel is used, the sealing gel may remain in contact with the retina continuing to inhibit or prevent reflux, and then be removed over time by the natural processes of the eye. A replacement fluid may be introduced into the vitreous chamber of the eye to replace vitreous humor removed as part of the retinal treatment.

Method 900, in conjunction with the systems and delivery devices described herein may facilitate the injection of therapeutic agents into subretinal space by a single surgeon. Because the system permits actuation of the injection of fluid by the surgeon holding the delivery device, such as by selecting a footswitch that is part of a control system, a second surgeon or an assistant may not be needed. Embodiments of delivery devices described herein may prevent or reduce the likelihood of puncturing of the retinal pigment epithelium (RPE) and may control the introduction of the therapeutic agents into the space to minimize sheering stresses and improve distribution, thereby improving efficacy.

Persons of ordinary skill in the art will appreciate that the embodiments encompassed by the present disclosure are not limited to the particular exemplary embodiments described above. In that regard, although illustrative embodiments have been shown and described, a wide range of modification, change, combination, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A retinal treatment device for delivering therapeutic agents to a target location within a retina, the retinal treatment device comprising:
    an outer tube having a lumen and having a distal end and a proximal end, the outer tube being sized to penetrate an eye to conduct retinal surgeries;
    a flexible tip sealingly coupled to the distal end of the outer tube, the flexible tip being configured to flexibly conform to a retinal surface when abutted against the retinal surface;
    an inner tube disposed within the lumen of the outer tube, the inner tube having a proximal end and a distal end, the distal end extending into the flexible tip, the inner tube being configured to extend from the flexible tip and penetrate through a portion of the retina into a subretinal space;
    at least one sealant channel in the flexible tip separate from the inner tube;
    a sealing gel configured to form a seal between the retinal treatment device and the retina to prevent reflux of therapeutic agents when the sealing gel is ejected from the flexible tip; and
    a chamber coupled to the proximal end of the inner tube, the chamber configured to receive a fluid containing therapeutic agents injectable through the inner tube into the subretinal space.

2. The retinal treatment device of claim 1, wherein the inner tube is configured to move relative to the outer tube and the flexible tip when a perforating tip of the inner tube is inserted into the retina.

3. The retinal treatment device of claim 1, further comprising a force moderation structure that moderates a force applied by a perforating tip of the inner tube.

4. The retinal treatment device of claim 3, wherein the force moderation structure is a spring.

5. The retinal treatment device of claim 4, wherein the spring is configured to prevent an applied force from exceeding a force required to perforate a retinal pigment epithelium layer of the eye.

6. The retinal treatment device of claim 1, wherein the inner tube is coupled to a drive mechanism that drives a perforating tip of the inner tube into the retina.

7. The retinal treatment device of claim 6, wherein the drive mechanism is a pneumatic or electric drive mechanism or a slider drive mechanism disposed on a hand-held controller.

8. The retinal treatment device of claim 1, wherein the first chamber defines a volume containing the therapeutic agent that is further defined by a plunger, the plunger being actuatable to inject a portion of the therapeutic agent from the volume through the inner tube into the subretinal space.

9. The retinal treatment device of claim 8, wherein the plunger is configured to be actuated electronically, pneumatically, or mechanically.

10. The retinal treatment device of claim 8, wherein the plunger is actuated by manual control or by computer control.

11. The retinal treatment device of claim 1, wherein the inner tube extends through a central channel of the flexible tip, the flexible tip comprising at least two sealant channels permitting the sealing gel to be ejected from the flexible tip.

12. The retinal treatment device of claim 11, wherein a volume of the sealing gel is disposed in a space between the inner tube and the outer tube.

13. The retinal treatment device of claim 1, wherein the inner tube comprises a chemically-treated interior surface.

14. The retinal treatment device of claim 1, wherein a distal portion of the inner tube comprises a curved section that curves when extended beyond the flexible tip to inject fluid horizontally into the subretinal space.

15. The retinal treatment device of claim 1, wherein the chamber is configured to receive a cartridge containing a pre-determined volume of fluid containing therapeutic agents.

16. The retinal treatment device of claim 1, further comprising a solution injected through the inner tube to form a bleb in the subretinal space prior to injecting the fluid containing therapeutic agents from the chamber.

17. A retinal treatment system for delivering therapeutic agents to a target location with a retina, the retinal treatment system comprising:
    a console having a control system;
    a handheld device coupled to the control system by a communication line, the handheld device comprising:
        an inner tube disposed within an outer tube and being axially moveable within the outer tube, the inner tube having a perforating tip at a distal end thereof configured to perforate an inner limiting membrane of the retina;
        a force moderation structure coupled to the perforating tip that moderates a force applied by the perforating tip of the inner tube, wherein the force moderation structure is configured to prevent an applied force from exceeding a force required to perforate a retinal pigment epithelium layer of the eye; and
        a chamber coupled to a proximal end of the inner tube, the chamber configured to receive a fluid containing therapeutic agents injectable from the perforating tip; and
    wherein the control system permits a user to maintain a position of the handheld device relative to the retina and activate an injection of a portion of the fluid through the inner tube into the retina.

18. The retinal treatment system of claim 17, wherein the control system comprises a footswitch having a pedal, a position of the pedal communicating a desired injection parameter to the console over a communication link between the control system and the footswitch.

19. The retinal treatment system of claim 18, wherein the desired injection parameter is a flow rate-, a pressure, or a sheer stress.

20. The retinal treatment system of claim 18, wherein an activation of the footswitch causes a predetermined volume of the fluid to be injected into the retina.

21. The retinal treatment system of claim 20, wherein the predetermined volume is set using an interface provided by the console.

22. The retinal treatment system of claim 17, further comprising an optical coherence tomography (OCT) system for measuring a thickness of the retina.

* * * * *